(12) United States Patent
Sumiya

(10) Patent No.: US 7,160,288 B2
(45) Date of Patent: Jan. 9, 2007

(54) OPHTHALMIC APPARATUS

(75) Inventor: Toshifumi Sumiya, Nukata-gun (JP)

(73) Assignee: Nidek Co., Ltd. (JP)

( * ) Notice: Subject to any disclaimer, the term of this patent is extended or adjusted under 35 U.S.C. 154(b) by 5 days.

(21) Appl. No.: 10/373,596

(22) Filed: Feb. 26, 2003

(65) Prior Publication Data

US 2003/0163122 A1   Aug. 28, 2003

(30) Foreign Application Priority Data

Feb. 27, 2002   (JP) ............................. 2002-052003

(51) Int. Cl.
*A61B 18/18* (2006.01)
*A61B 3/10* (2006.01)

(52) U.S. Cl. .................. 606/4; 606/5; 606/10; 351/211

(58) Field of Classification Search ................ 606/4, 606/5, 10–12; 351/208–212
See application file for complete search history.

(56) References Cited

U.S. PATENT DOCUMENTS

| | | | |
|---|---|---|---|
| 4,620,318 A | | 10/1986 | Hill |
| 5,465,123 A | * | 11/1995 | Iijima .......................... 351/208 |
| 5,474,548 A | | 12/1995 | Knopp |
| 5,684,562 A | * | 11/1997 | Fujieda ........................ 351/212 |
| 5,757,462 A | | 5/1998 | Nanjo |
| 5,777,719 A | * | 7/1998 | Williams et al. ............. 351/212 |
| 5,907,388 A | | 5/1999 | Fujieda |
| 6,033,075 A | | 3/2000 | Fujieda et al. |
| 6,086,204 A | | 7/2000 | Magnante |
| 6,159,202 A | * | 12/2000 | Sumiya et al. ................. 606/4 |
| 6,217,570 B1 | | 4/2001 | Nevyas |
| 6,234,978 B1 | | 5/2001 | Mihashi et al. |
| 6,245,058 B1 | | 6/2001 | Suzuki |
| 6,508,812 B1 | * | 1/2003 | Williams et al. ................ 606/5 |
| 6,585,723 B1 | * | 7/2003 | Sumiya ......................... 606/5 |
| 6,712,808 B1 | * | 3/2004 | Fujieda ......................... 606/4 |
| 2002/0049430 A1 | | 4/2002 | Kondo et al. |

FOREIGN PATENT DOCUMENTS

| | | |
|---|---|---|
| EP | 0 933 060 A1 | 8/1999 |
| EP | 0 933 060 A1 * | 8/2001 |
| JP | 10-305013 A1 | 11/1998 |
| JP | 11-128264 A1 | 5/1999 |
| JP | 11-342152 A1 | 12/1999 |
| WO | WO 01/89373 A2 | 11/2001 |

OTHER PUBLICATIONS

Partial EPO Search Report, mailed Oct. 19, 2004.

* cited by examiner

*Primary Examiner*—A. Farah
(74) *Attorney, Agent, or Firm*—Rader Fishman & Grauer PLLC; Ronald P. Kananen

(57) ABSTRACT

An ophthalmic apparatus capable of guiding the visual axis of an eye to be examined, obtaining information about the visual axis, and performing measurement of optical characteristics of an eye such as wavefront aberration or laser refractive surgery with reference to the visual axis. The apparatus is provided with a target presenting optical system for guiding a visual axis of a patient's eye, and the presenting optical system has an optical axis of presentation and is provided with a first target and a second target located on the eye's side relative to the first target both on the optical axis of presentation, where the optical axis of presentation coincides with the visual axis when the eye fixates so as to make the first target coincide with the second target.

4 Claims, 4 Drawing Sheets

OPHTHALMIC APPARATUS

BACKGROUND OF THE INVENTION

1. Field of the Invention

The present invention relates to an ophthalmic apparatus.

2. Description of Related Art

In recent years, there have been more and more cases of performing laser refractive surgery in which a corneal stroma is ablated with an excimer laser beam to change a curvature of a corneal anterior surface for correcting a refractive error of an eye. Lately, a new type of surgery has begun to be performed to seek further improvement in visual acuity by measuring wavefront aberration of an eye and controlling ablation to correct the aberration. In this type of laser refractive surgery, wavefront aberration or a corneal shape is measured before the surgery.

However, the apparatuses for measuring wavefront aberration or a corneal shape take measurements with reference to a line of sight of an eye linking the center of the entrance pupil to a fixation point, or with reference to a keratometric axis, not a visual axis of the eye linking the central fovea to the fixation point through nodal points. In addition, a conventional laser corneal surgery apparatus performs ablation with reference to an approximate center of the pupil (if the eye to be operated on is fixating a fixation light source located on an optical axis, it means that the ablation is performed with reference to the line of sight), not the visual axis, either. It follows then that the measurement is made based on an axis different from the visual axis given when the eye is actually looking at an object, and that the wavefront aberration is corrected based on that different axis, and an expected visual acuity may not be obtained if the difference is large.

SUMMARY OF THE INVENTION

The present invention has been made in view of the above circumstances and has an object to overcome the above problems and to provide an ophthalmic apparatus capable of guiding a visual axis of an eye and obtaining information about the visual axis. In addition, the present invention also has an object to provide an ophthalmic apparatus that enables measurement of optical characteristics of an eye such as wavefront aberration or laser refractive surgery to be performed with reference to the visual axis.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus is provided with a target presenting optical system for guiding the visual axis of a patient's eye. The presenting optical system has an optical axis of presentation, and is provided with a first target and a second target located on the eye's side relative to the first target both on the optical axis of presentation, where the optical axis of presentation coincides with the visual axis when the eye fixates so as to make the first target coincide with the second target.

In another aspect of the present invention, an ophthalmic apparatus is provided with a target presenting optical system for guiding the visual axis of a patient's eye and a measurement optical system for measuring an optical characteristic of the eye including at least one of wavefront aberration, distribution of corneal curvature and distribution of eye refractive power. The presenting optical system has an optical axis of presentation, and is provided with a first target and a second target located on the eye's side relative to the first target both on the optical axis of presentation, where the optical axis of presentation coincides with the visual axis when the eye fixates so as to make the first target coincide with the second target. The measurement optical system has an optical axis of measurement coaxial with the optical axis of presentation.

Yet, in another aspect of the present invention, an ophthalmic apparatus is provided with a target presenting optical system for guiding the visual axis of a patient's eye, an irradiation optical system for irradiating a cornea of the eye with a laser beam for refractive surgery, input means for inputting corneal ablation data obtained with reference to the visual axis, and control means for controlling laser irradiation based on the inputted corneal ablation data. The presenting optical system has an optical axis of presentation, and is provided with a first target and a second target located on the eye's side relative to the first target both on the optical axis of presentation, where the optical axis of presentation coincides with the visual axis when the eye fixates so as to make the first target coincide with the second target. The irradiation optical system has an optical axis of irradiation coaxial with the optical axis of presentation.

BRIEF DESCRIPTION OF THE DRAWINGS

The accompanying drawings, which are incorporated in and constitute apart of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
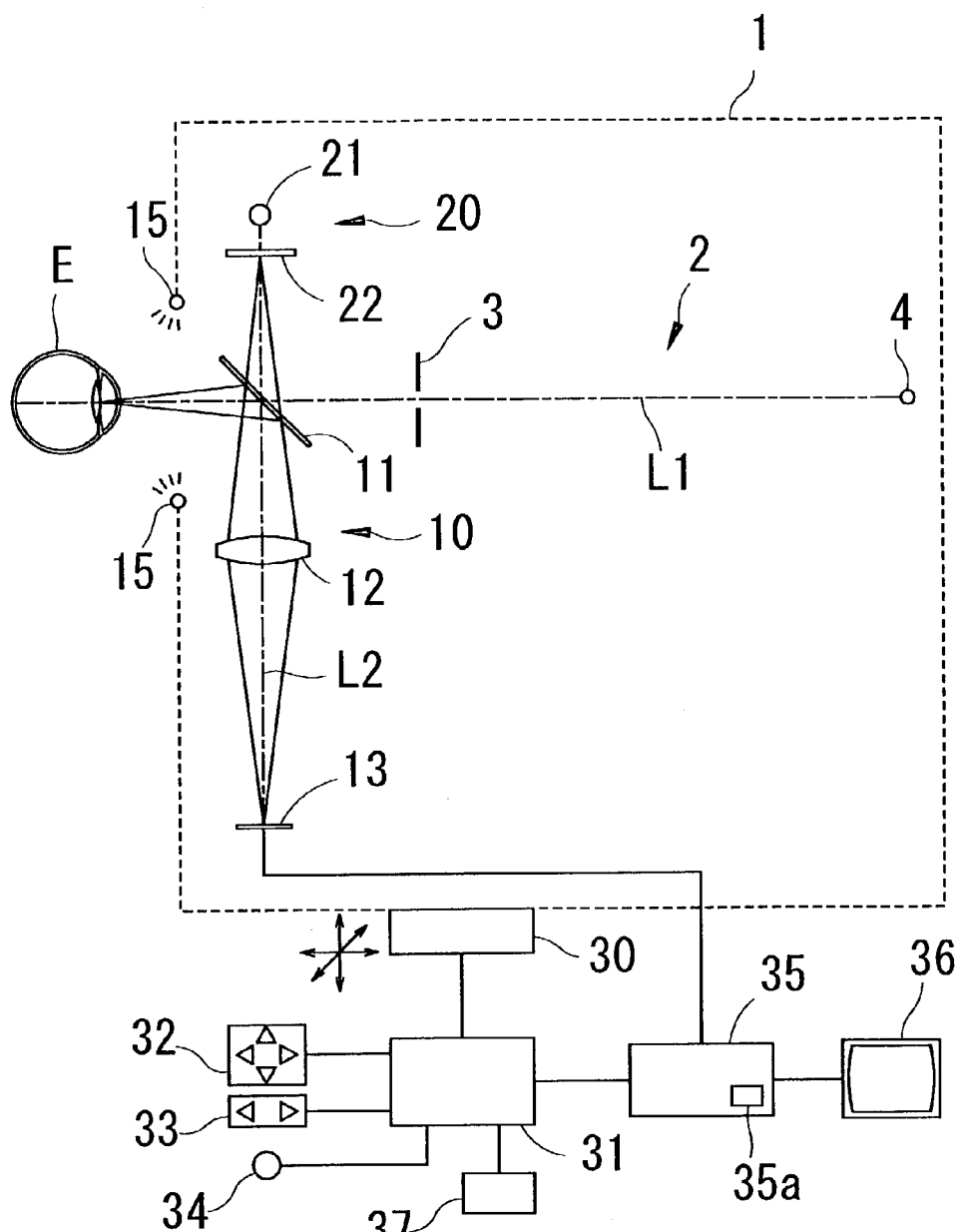
FIG. 1 is a view showing a schematic configuration of an ophthalmic apparatus consistent with the present invention.

A detailed description of one preferred embodiment of an ophthalmic apparatus embodying the present invention will now be given referring to the accompanying drawings. FIG. 1 shows a schematic configuration of the ophthalmic apparatus consistent with the present invention.

Figure 2:
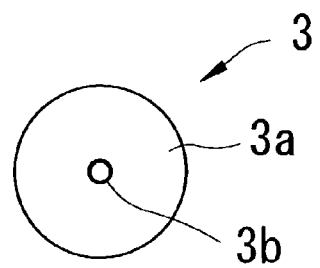
FIG. 2 is a view illustrating an aperture plate shown in FIG. 1.

Provided on an optical axis L1 of a fixation target presenting optical system 2 are an aperture plate 3 and a visible fixation light source 4 as a fixation point. The aperture plate 3 is provided with an aperture 3b formed as a small-diameter, ring-shaped opening mark in a transparent member 3a as shown in FIG. 2, and is placed at such a distance as to be visible to an eye E to be examined. The optical axis L1 passes through the center of the aperture 3b (the member 3a). The fixation light source 4 is placed at a certain distance far from the aperture plate 3. A lens may be placed between the aperture plate 3 and the fixation light source 4 to secure an optical distance. The eye E fixates the fixation light source 4 through the aperture 3b so that the fixation light source 4 may coincide with the center of the aperture 3b. Therefore, the aperture plate 3 is placed at a sufficient distance from the eye E, and the fixation light source 4 serves as a first fixation target with the aperture 3b as a second fixation target. It should be noted that the aperture plate 3 may be formed of a small aperture only, but the formation shown in FIG. 2 can make it easier to guide the eye E to fixate the fixation light source 4 through the aperture 3b. Alternatively, the aperture 3b may also be formed as a small-diameter, circular-shaped shielding mark for guiding the eye fixation so that the mark may hide the fixation light source 4 from view.

A image-pickup (photographing) optical system 10 is provided with a dichroic mirror 11 placed on the optical axis L1 between the aperture plate 3 and the eye E, an image-pickup lens 12 and a CCD camera 13 as an image-pickup element both placed on an optical axis L2 (The optical axis L2 coincides with an optical axis of the lens 12). The dichroic mirror 11 transmits visible light and reflects near infrared light. The dichroic mirror 11 makes the optical axis L2 of the image-pickup optical system 10 coaxial with the optical axis L1. The camera 13 has a sensitivity to the wavelengths ranging from the visible region to the near infrared region. The image-pickup lens 12 forms an image of the pupil of the eye E on the camera 13, and the pupil of the eye E and the camera 13 have a relationship conjugate with each other with respect to the image-pickup lens 12. Near infrared light sources 15 illuminate an anterior segment of the eye E including the pupil. Then the near infrared light reflected from the anterior segment is reflected by the dichroic mirror 11, and enters the image-pickup lens 12, so that the image of the anterior segment is formed on the camera 13.

A reticle projection optical system 20 is provided with a visible light source 21 and a reticle plate 22 both placed on an optical axis L3. The dichroic mirror 11 makes the optical axis L3 of the reticle projection system 20 coaxial with the optical axis L2. The reticle plate 22 is provided with a reticle pattern in the form of cross-hairs or the like of which the center is easy to recognize, and the optical axis L2 passes through the center of the reticle pattern. The visible light transmitted through the reticle plate 22 is also transmitted through the dichroic mirror 11 and the image-pickup lens 12 to form an image of the reticle pattern on the camera 13. This indicates where the optical axis L2 is located in the image of the anterior segment formed on the camera 13. The location of the optical axis L2 corresponds to a visual axis given when the eye E fixates the fixation light source 4 through the aperture 3b, indicating where the visual axis is located.

The above-mentioned optical systems are stored in an optometric part 1 which is moved three-dimensionally, up/down, rightward/leftward and forward/backward, by a driving part 30. The driving part 30 connects with a system control part 31 to which a switch 32 for moving the optometric part 1 up/down and rightward/leftward, a switch 33 for moving the optometric part 1 forward/backward, and an image-pickup switch 34 are connected. The output of the camera 13 connects with an image processing part 35 including an image memory 35a, and a monitor (display) 36 connects with the image processing part 35. Data are inputted and outputted through a data input/output part 37.

In the above-described configuration, the camera 13 picks up an image of the anterior segment of the eye E illuminated by the light source 15, and the image is displayed on the monitor 36. An examiner observes the image of the anterior segment displayed on the monitor 36, and moves the optometric part 1 forward/backward using the switch 33 so that the iris of the eye E may come into focus, thereby performing fore-and-aft alignment. The alignment may be performed automatically through image processing conducted by the image processing part 35.

In addition, an examinee operates the switch 32 to move the optometric part 1 up/down and rightward/leftward in order that the eye E may observe the fixation light source 4 through the aperture 3b. The examiner may operate the switch 32 according to the response from the examinee. Making the eye E fixate the fixation light source 4 seen at the center of the aperture 3b through that aperture brings the visual axis of the eye E into agreement with the optical axis L1.

Once the fixation of the eye E has been guided as described above, the examiner depresses the switch 34 to pick up the image of the anterior segment including the pupil using the camera 13. At the same time, the camera 13 also picks up the image of the reticle pattern formed by the visible light from the reticle projection optical system 20. The image picked up by the camera 13 is stored in the image memory 35a.

Figure 3:
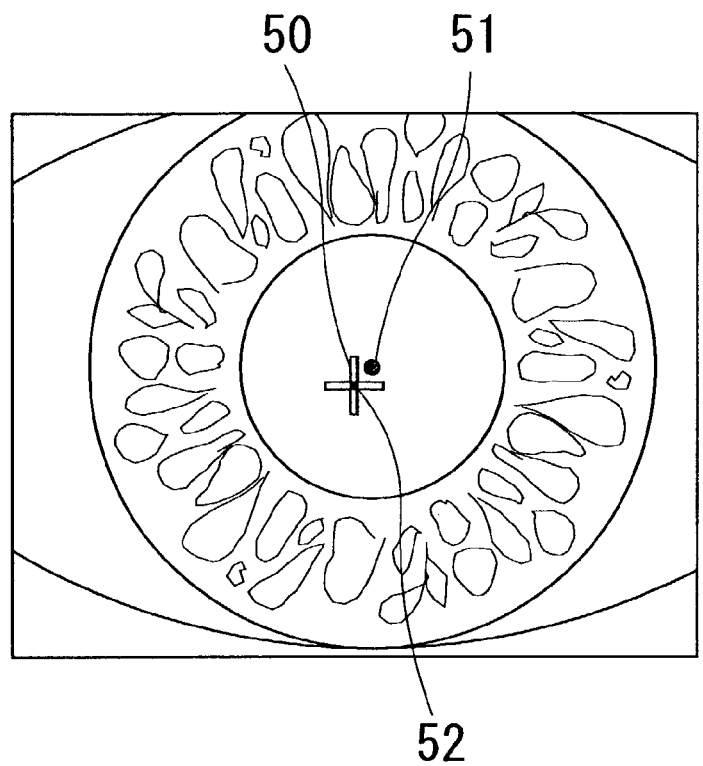
FIG. 3 is a view showing an example of an image picked up by a CCD camera and displayed on a monitor.

FIG. 3 shows an example of the image picked up by the camera 13 and displayed on the monitor 36, where a reticle pattern image 50 formed by the reticle projection optical system 20 is also picked up along with the image of the pupil. The image processing part 35 extracts a pupil edge from the image of the anterior segment to detect the center of the pupil. Under one method, for example, the pupil center may be detected as an intersection of the diagonal lines of a rectangle confined by two lateral lines and two vertical lines all of which are tangent to the pupil edge. Of course, other methods may also be applicable, but it is preferred that the method conform to the detection of the pupil center which is used as a reference point at the time of measuring wavefront aberration or performing laser refractive surgery. In FIG. 3, a point 51 indicates the detected pupil center.

In addition, the image processing part 35 obtains a reticle center 52 in the reticle pattern image 50. And, the reticle center 52 represents the location of the visual axis which passes within a plane of the pupil. Therefore, the amount of deviation ($\Delta x$, $\Delta y$) of the visual axis passing within the pupil plane with respect to the pupil center is detected based on each of the positions of the reticle center 52 and the pupil center 51. The deviation amount ($\Delta x$, $\Delta y$) of the visual axis is utilized when an amount of ablation for laser refractive surgery is calculated from the measurement data about wavefront aberration. It should be noted that the reticle projection optical system 20 is not necessarily needed if the position of the optical axis L2 on the camera 13 is known in advance.

As for the measurement of wavefront aberration, the so-called Hartmann-Shack wavefront sensor is typically known, in which an image of a light source is projected onto the fundus of an eye to be examined, the light reflected from the fundus forms an image on the image sensor through a multiple-microlens array placed at a position conjugate with the pupil, and the wavefront of the light refracted by the cornea is measured based on information about the formed image. The optical-system configuration of this sensor is described in U.S. Pat. No. 6,086,204 and U.S. Pat. No. 6,234,978 (Japanese Patent Application Unexamined Publication No. Hei 10-305013) and others. In such an optical system, usually, a result of the measurement may be obtained with reference to a line of sight passing through the pupil center. And, data about a corneal ablation amount for correcting wavefront aberration is obtained based on the result of the wavefront aberration measurement.

Figure 4:
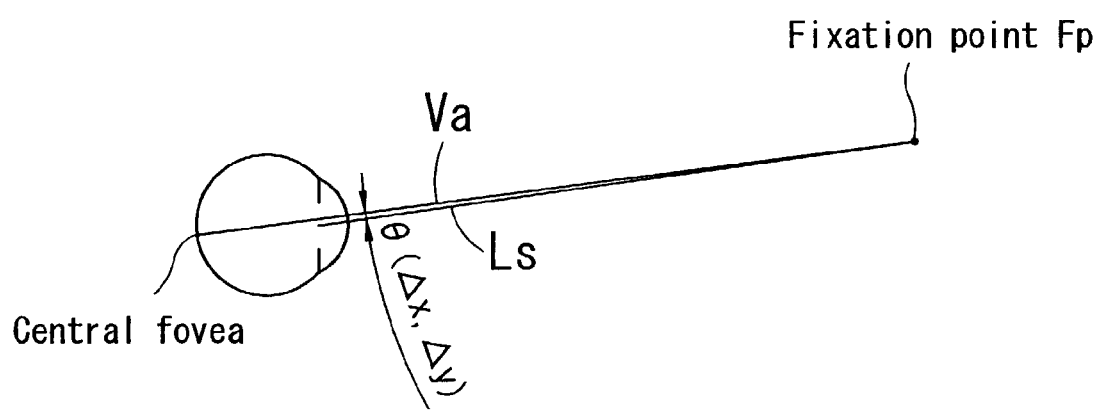
FIG. 4 is a view showing a relationship between a visual axis and a line of sight.

Nevertheless, the wavefront aberration is measured with reference to a line of sight LS as shown in FIG. 4. It follows that the ablation amount based on the measured wavefront aberration is not exactly commensurate with correction of the wavefront aberration to be made with reference to a visual axis Va. Therefore, the data obtained from the measurement of the wavefront aberration with reference to the line of sight Ls is converted to those with reference to the visual axis Va. For such conversion, first, the angle θ ($\Delta x'$, $\Delta y'$) between the line of sight Ls and the visual axis Va is found based on the deviation amount ($\Delta x$, $\Delta y$) of the visual axis Va obtained in the above-described manner and a distance from the fixation light source (a fixation point Fp) at the time of measuring the wavefront aberration, and these values are then utilized for the conversion. And, in the case of performing laser refractive surgery with reference to the line of sight Ls, the ablation amount with reference to the visual axis Va is calculated based on the measurement data with reference to the visual axis Va, and the calculated ablation amount with reference to the visual axis Va is converted to those with reference to the line of sight Ls based on the deviation amount ($\Delta x$, $\Delta y$) of the visual axis and the angle θ ($\Delta x'$, $\Delta y'$). Such a calculation capability may be included in the control part 31 or a computer where the deviation amount ($\Delta x$, $\Delta y$) of the visual axis has been outputted (e.g. a computer on the side of the laser refractive surgery apparatus) Data are inputted and outputted via the input/output part 37.

Figure 5:
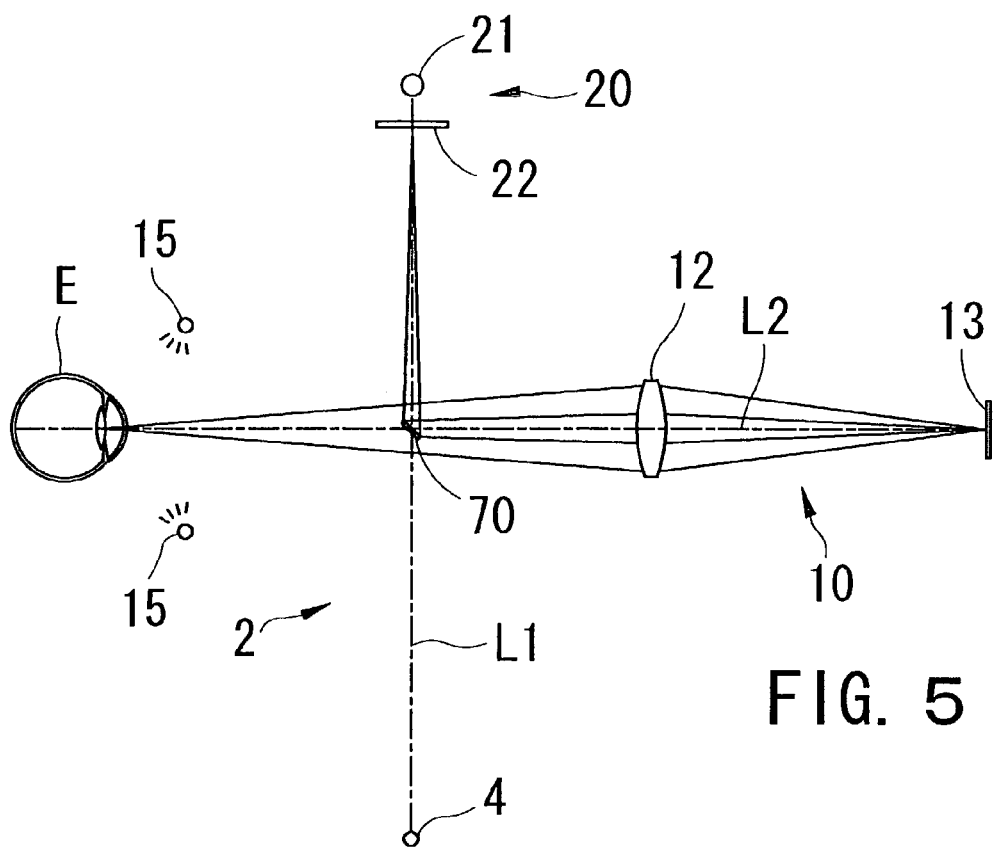
FIG. 5 is a view showing a modification of optical systems included in the present apparatus.

FIG. 5 shows a modification of the fixation target presenting optical system. In this modification, instead of the aperture plate 3, a micro mirror 70 is used to bend the optical axis L1 of the fixation target presenting optical system 2 into 90° and the image-pickup optical system 10 is provided in front of the eye E. In this configuration, the optical axis L1 and the visual axis may also be made to coincide with each other by making the eye E fixate the fixation light source 4 located in the reflecting direction of the mirror 70 via the mirror 70.

It should be noted that, in the aforementioned configuration, the sizes of the aperture 3b and the mirror 70 and the distance between the eye E and the fixation light source 4 are determined during the design phase in relation to the tolerance for making the visual axis of the eye E and the optical axis L1 coincide with each other.

Figure 6:
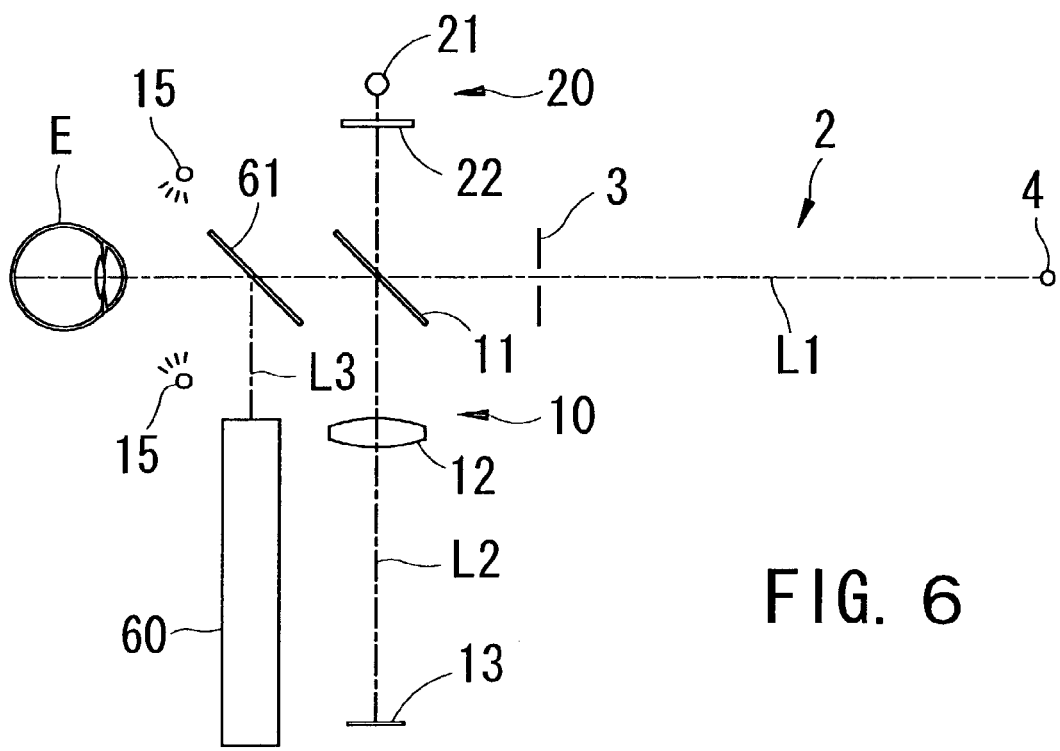
FIG. 6 is a view showing an example in the case of incorporating a measurement optical system into the apparatus.

In addition, in the above description, wavefront aberration is measured using a different ophthalmic apparatus, but FIG. 6 shows an example of incorporating a measurement optical system into the apparatus. In FIG. 6, reference numeral 60 denotes a measurement optical system for measuring wavefront aberration (the one described in U.S. Pat. No. 6,086,204 and U.S. Pat. No. 6,234,978 (Japanese Patent Application Unexamined Publication No. Hei 10-305013) of the present applicant or others may be used), and L4 denotes a measurement optical axis of that system. The optical axis L4 is made coaxial with the optical axis L1 of the fixation target presenting optical system 2 by a beam splitter 61. In this case, wavefront aberration may be measured with reference to the visual axis. Therefore, in laser refractive surgery, the deviation amount ($\Delta x$, $\Delta y$) of the visual axis and the angle θ ($\Delta x'$, $\Delta y'$) may be used to calculate the ablation amount with reference to the line of sight.

It should be noted that the measurement of the optical characteristics of an eye, which are factors for determining the ablation amount for laser refractive surgery, is not limited to the measurement of wavefront aberration, and also includes the measurement of a corneal shape and eye refractive power; the former of which measures a distribution of corneal curvature over a wide range of a cornea, and the latter of which measures a distribution of refractive power over a wide range of the cornea (see U.S. Pat. No. 6,033,075, Japanese Patent Application Unexamined Publication No. Hei 11-342152). These measurements may be made with reference to the visual axis by combining the optical systems shown in FIG. 1 and making the measurement optical axis therein coaxial with the optical axis L1.

Figure 7:
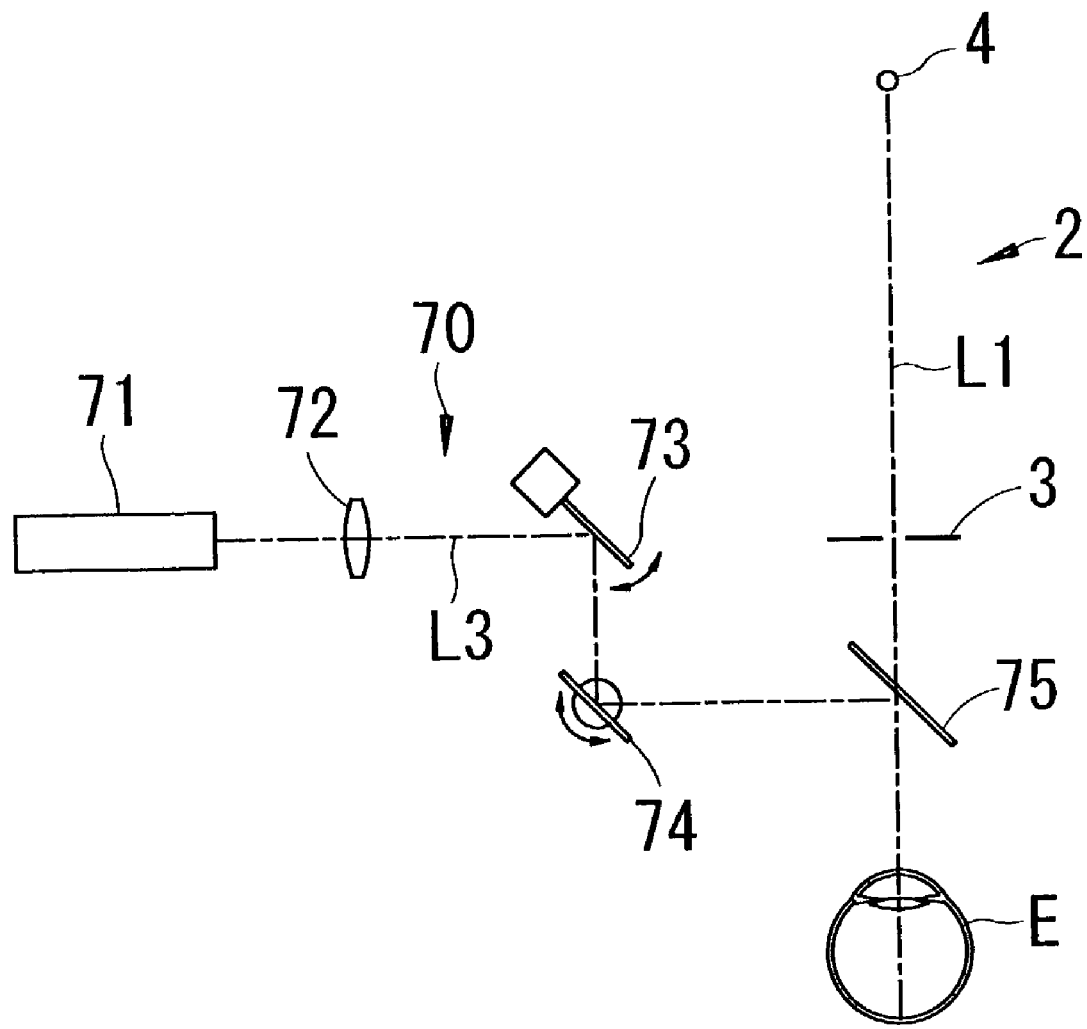
FIG. 7 is a view showing an example of providing a laser refractive surgery apparatus with a fixation target presenting optical system consistent with the present invention.

Furthermore, if laser refractive surgery is performed with reference to the visual axis, it becomes unnecessary that the measurement data such as wavefront aberration and the ablation data both obtained with reference to the visual axis be restored to those obtained with reference to the line of sight. FIG. 7 shows an example of providing the above-described fixation target presenting optical system 2 in an apparatus for performing laser refractive surgery. In this apparatus, a laser irradiation optical system 70 includes an excimer laser source 71, a converging lens 72, and two galvano-mirrors 73 and 74, and a dichroic mirror 75 reflecting an excimer laser beam and transmitting visible light makes an optical axis L5 of the irradiation optical system 70 and the optical axis L1 of the fixation target presenting optical system 2 coaxial with each other.

The converging lens 72 changes the laser beam from the laser source 71 into a small spot beam of about 1-mm diameter on the cornea of the eye E to be operated on. The laser beam scans the cornea by means of the two galvano-mirrors 73 and 74, and each scanning position and duration of the laser irradiation are controlled based on ablation amount data, thereby correcting wavefront aberration. During the scanning, if the eye E is made to fixate the fixation light source 4 through the aperture 3b so that they are seen in agreement with each other, refractive surgery may be performed with reference to the visual axis. It should also be noted that the laser irradiation optical system 70 is not limited to that configured as shown in FIG. 7, and may be applied to various configurations, for example, as described in U.S. Pat. No. 6,245,058, Japanese Patent Application Unexamined Publication No. Hei 11-128264.

As described up to this point, according to the present invention, the visual axis of an eye to be examined may be guided and information about the visual axis may be obtained, which can be utilized to enable laser refractive surgery with high accuracy. In addition, optical characteristics of an eye such as wavefront aberration may be measured and laser refractive surgery may be performed with reference to the visual axis.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:
a presenting optical system presenting a fixation target for guiding a visual axis of a patient's eye with accuracy, the presenting optical system including:
a first optical axis,
one of a small aperture and a micro mirror as a first fixation target, which is placed at a first position on the first optical axis; and
a fixation light source as a second fixation target, which is placed at a second position on the first optical axis separate from the first position,
wherein the visual axis coincides with the first optical axis by making the eye fixate the second fixation target via the first fixation target;
an image-pickup optical system picking up a front image of an anterior segment of the eye including a pupil, the image-pickup optical system including a second optical axis having a predetermined positional relationship with the first optical axis; detecting means for detecting a deviation amount between a pupil center position of the eye and a pupil position which the visual axis passes through by processing an image signal of the front image of the anterior segment; and
angle calculating means for calculating an angle between a line of sight of the eye and the visual axis based on the detected deviation amount.

2. The ophthalmic apparatus according to claim 1, further comprising:
input means for inputting measurement data with reference to the line of sight of at least one of wavefront aberration, distribution of corneal curvature and distribution of eye refractive power of the eye which is a factor for determining an amount of corneal ablation of the eye; and
corneal ablation amount calculating means for converting the inputted measurement data with reference to the line of sight into measurement data with reference to the visual axis based on the detected deviation amount and the calculated angle, and calculating an amount of corneal ablation with reference to the line of sight based on the converted measurement data with reference to the visual axis, the detected deviation amount and the calculated angle.

3. The ophthalmic apparatus according to claim 1, further comprising
a measurement optical system obtaining measurement data with reference to the visual axis of at least one of wavefront aberration, distribution of corneal curvature and distribution of eye refractive power of the eye which is a factor for determining an amount of corneal ablation of the eye, the measurement optical system including a third optical axis having a predetermined positional relationship with the first optical axis.

4. The ophthalmic apparatus according to claim 3, further comprising corneal ablation amount calculating means for calculating an amount of corneal ablation with reference to the line of sight based on the obtained measurement data with reference to the visual axis, the detected deviation amount and the calculated angle.

* * * * *